(12) United States Patent
Corma Canos et al.

(10) Patent No.: US 10,442,753 B2
(45) Date of Patent: Oct. 15, 2019

(54) DIRECT AMINATION OF HYDROCARBONS

(71) Applicant: Huntsman International LLC, The Woodlands, TX (US)

(72) Inventors: Avelino Corma Canos, Valencia (ES); Patricia Concepcion Heydorn, Valencia (ES)

(73) Assignee: HUNTSMAN INTERNATIONAL LLC, The Woodlands, TX (US)

( * ) Notice: Subject to any disclaimer, the term of this patent is extended or adjusted under 35 U.S.C. 154(b) by 0 days.

(21) Appl. No.: 15/561,708

(22) PCT Filed: Feb. 23, 2016

(86) PCT No.: PCT/EP2016/053743
§ 371 (c)(1),
(2) Date: Sep. 26, 2017

(87) PCT Pub. No.: WO2016/155948
PCT Pub. Date: Oct. 6, 2016

(65) Prior Publication Data
US 2018/0086690 A1 Mar. 29, 2018

(30) Foreign Application Priority Data
Apr. 2, 2015 (EP) .................................. 15162425

(51) Int. Cl.
| | |
|---|---|
| *C07C 209/02* | (2006.01) |
| *B01J 6/00* | (2006.01) |
| *B01J 29/84* | (2006.01) |
| *B01J 37/02* | (2006.01) |
| *B01J 37/18* | (2006.01) |
| *C07C 211/46* | (2006.01) |
| *B01J 29/83* | (2006.01) |
| *B01J 37/14* | (2006.01) |

(52) U.S. Cl.
CPC .............. *C07C 209/02* (2013.01); *B01J 6/001* (2013.01); *B01J 29/83* (2013.01); *B01J 29/84* (2013.01); *B01J 37/0201* (2013.01); *B01J 37/18* (2013.01); *C07C 211/46* (2013.01); *B01J 37/14* (2013.01); *B01J 2229/183* (2013.01); *B01J 2229/186* (2013.01); *B01J 2231/44* (2013.01); *B01J 2523/55* (2013.01)

(58) Field of Classification Search
None
See application file for complete search history.

(56) References Cited

U.S. PATENT DOCUMENTS

2009/0292144 A1  11/2009  Anders et al.

FOREIGN PATENT DOCUMENTS

| CN | 103408434 A | 11/2013 |
|---|---|---|
| DE | 19634110 A1 | 2/1998 |
| WO | 2000009473 A1 | 2/2000 |

OTHER PUBLICATIONS

DE-19634110 machine translation (from Google patents, Dec. 25, 2018).*
Olsen, Atlas of Zeolite Framework Types, 2001, pp. 1-20 attached.*
Maurelli et al. J Phys. Chem C. 2014, 118, 19879-19888.*

* cited by examiner

*Primary Examiner* — Clinton A Brooks
(74) *Attorney, Agent, or Firm* — Huntsman International LLC; Robert Diaz

(57) ABSTRACT

Process for preparing aminated aromatic hydrocarbons that may be substituted comprising the steps of reacting an aromatic hydrocarbon with ammonia in the presence of a catalyst having a crystalline microporous structure wherein the catalyst comprises vanadium aluminophosphate molecular sieve (VAPO) and/or aluminophosphate molecular sieve (AlPO) and wherein the catalyst is preferably impregnated with nickel and/or copper, and wherein the aromatic hydrocarbon may be substituted.

12 Claims, No Drawings

DIRECT AMINATION OF HYDROCARBONS

CROSS-REFERENCE TO RELATED APPLICATIONS

This application is the National Phase of International Application PCT/EP2016/053743 filed Feb. 23, 2016 which designated the U.S. and which claims priority to European Application Serial. No. 15162425.1 filed Apr. 2, 2015. The noted applications are incorporated herein by reference.

The invention relates to a process for direct amination of hydrocarbons that may be substituted, preferably aromatic hydrocarbons that may be substituted using ammonia for amination in the presence of a catalyst which catalyzes the amination. More in particular, the invention relates to the direct amination of benzene to prepare aniline.

Aniline is currently manufactured using two separate manufacturing steps, namely nitration of benzene to nitrobenzene followed by hydrogenation to aniline. Although both reactions are operated efficiently in today's commercial processes, there are still significant capital and variable cost benefits to be obtained if benzene can be converted to aniline in a single process step. Direct amination of hydrocarbons such as benzene via catalysts are also known in the art. Such processes are described in e.g. DE19634110 where a reducible metal oxide catalyst in the presence of an oxidant is used to form aniline from benzene. Also the use of cataloreactants for direct amination of benzene with ammonia is described. E.g. US 2009/0292144 describes the reactivity of a mixed metal oxide catalyst for direct amination of benzene, where the catalyst was prepared by coprecipitation techniques and includes Ni, Cu, Zr, Mo as metal oxides. Cataloreactants first consume the hydrogen generated by the amination reaction and drive the reaction equilibrium toward the product. The catalyst is then regenerated in a separate step.

The processes described in the prior art provide direct amination where the selectivity and the space time yield are low. In addition, the catalysts used for direct amination need to be activated at high temperatures, which adversely affects the required reaction and stimulates the decomposition of ammonia into nitrogen and hydrogen. This side reaction upsets the reaction equilibrium adversely and reduces the aniline yield drastically.

It is therefore an object to provide a process for direct amination of hydrocarbons that may be substituted where the selectivity for making the aminated hydrocarbon is high while at the same time high space time yield is achieved. In addition it is an object that the decomposition of ammonia used in the direct amination is limited to a minimum, or that the ammonia does not decompose at all.

These objects, amongst others, are met, at least partially, by a process according to the claims. In particular, these objects, are met by a process for preparing aminated aromatic hydrocarbons that may be substituted comprising the steps of reacting an aromatic hydrocarbon with ammonia in the presence of a catalyst having a crystalline microporous structure wherein the catalyst comprises vanadium aluminophosphate molecular sieve (VAPO) or aluminophosphate molecular sieve (AlPO), preferably impregnated with nickel and/or copper, and wherein the aromatic hydrocarbon may be substituted. It has been found that these catalysts, enhance the performance of amination. These catalysts are able to aminate hydrocarbons in the presence of ammonia wherein the selectivity of the reaction is high and the space time yield of the aminated hydrocarbons that is achieved is high. Furthermore, these catalysts do not cause the decomposition of ammonia in hydrogen and nitrogen as a side reaction. In addition, it has been found that especially VAPO provides high yield of aniline when benzene is aminated with ammonia. In addition, the catalyst can be regenerated several times and no ammonia decomposition occurs during the amination reaction.

According to this invention, a catalyst having a crystalline microporous structure, means that it is possible to provide an X-ray diffraction pattern of the catalyst and that the catalyst has pores that are smaller than 20 Å.

A molecular sieve catalyst is generally a catalyst with a microporous structure composed of crystalline aluminosilicate and belongs to a class of materials known as zeolites. Also non-zeolite molecular sieve catalysts exist and comprise the crystalline aluminophosphates and aluminosilicaphosphates. The molecular sieve catalysts according to this invention are crystalline aluminophosphates (AlPO), and aluminophosphates that are substituted with vanadium (VAPO). The molecular sieve catalyst can also include other components such as binders, fillers, like clay, and optionally other catalytically active agents such as rare earth metal oxides, transition metal oxides, or noble metal components.

According to this invention, with selectivity is meant the amount of hydrocarbons that are converted to the desired aminated hydrocarbons per part of total hydrocarbons that have reacted. As example, in case the hydrocarbon is benzene, selectivity means the amount of benzene that is converted to aniline per total amount of benzene that has reacted. When the number is higher, the selectivity is better. When the selectivity is low, this means that more side products are formed. Typical side products in the conversion of benzene to aniline in the presence of ammonia are toluene, benzonitrile, biphenyl and carbazole.

Without being bound to a theory, it is thought that vanadium species in an amination of benzene can activate the ammonia by increasing the electrophilicity so that a nucleophilic attack of the benzene is enabled. Further framework oxygen in the solid catalyst can oxidize the produced hydrogen to water. In this way the reaction equilibrium is shifted to the product side.

In one preferred embodiment, the molecular sieve catalyst according to the invention is impregnated with nickel and/or copper. More preferably the molecular sieve catalyst is impregnated with nickel oxides and/or copper oxides. Most preferably, the catalysts are impregnated with both nickel oxide and copper oxide. When the AlPO and VAPO catalysts are impregnated with nickel and copper oxides, the yield of the converted hydrocarbons is even higher than when no nickel or copper oxides are used or when only nickel or only copper is used. Also the selectivity of the reaction is much higher. Preferably the nickel content is between 1 and 30 wt %, more preferably between 1 and 10 wt % compared to the total weight of the catalyst. Preferably the copper content is between 1 and 30 wt %, more preferably between 1 and 10 wt % compared to the total weight of the catalyst. An example of a suitable catalyst is a VAPO support or an AlPO support that is impregnated with 7.7 wt % nickel and 3.8 wt % copper.

In another embodiment, the molecular sieve catalyst according to the invention is further treated. This treatment can be calcination or reduction. Calcination can be performed using e.g. air or oxygen. Reduction can occur using e.g. molecular hydrogen, hydrazine, borohydride salts (e.g. $LiBH_4$, $NaBH_4$,) or ammonia.

In one embodiment, the catalyst is reduced in the presence of molecular hydrogen. Preferably the catalyst is activated via reduced in situ in the reactor. The reduction with hydrogen preferably occurs at a temperature between 100° C. and 300° C., more preferably between 150° C. and 250° C., most preferably at about 200° C. The reduction is preferably performed during between 40 and 150 minutes, preferably between 60 and 90 minutes, more preferably around 80 minutes. It has been found that a reduction time of 80 minutes may lead to an increased yield. The reduction with hydrogen reduces the metals in the catalyst.

In another embodiment the catalyst is calcined with air, preferably at a temperature between 300 and 800° C., more preferably between 400 and 600° C., even more preferably at around 500° C. The calcination with air is preferably performed during between 40 and 150 minutes, preferably between 50 and 80 minutes, more preferably around 60 minutes. The calcination with oxygen oxidizes the metals in the catalyst.

Preferably, when the catalyst comprises VAPO the catalyst is reduced with molecular hydrogen. This embodiment provides very good results in selectivity and yield.

The VAPO and AlPO catalysts that can be used in the process of the invention have a microporous structure. Preferably the microporous structure is defined by the framework type code provided by the International Zeolite Association selected from the group consisting of AFI, AEL, ATO, AEI, AET, AFN, AFO, AFT, ATV, CHA, ERI, LEV, SOD, and VFI. The most preferred catalysts for the invention are those having a framework type code of AFI, AEL or ATO. These correspond to AlPO-5, AlPO-11 and ALPO-31, respectively, for the AlPO catalysts and VAPO-5, VAPO-11 and VAPO-31, respectively, for the VAPO catalysts.

The aromatic hydrocarbons may be substituted. Substituted aromatic hydrocarbons may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyan, methylsulfonylamino, alkoxy, acyloxy, nitro, and lower haloalkyl. The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyan, methylsulfonylamino, alkoxy, alkyl, aryl, aralkyl, acyloxy, nitro, and lower haloalkyl. Examples of aromatic hydrocarbons that may be substituted are benzene, biphenyl, naphthalene, anthracene, chrysene, pheanthrene, pyrene, indene, alkylated benzenes such as toluene, o-, m-, p-xylene, ethylbenzene, o-, m-, p-diethylbenzene, propylbenzene, cumene, mesitylene, hydroxybenzenes such as phenol, o-, m-, p-cresol, xylenols; alkoxybenzenes, such as anisole, ethoxybenzene, propoxybenzene; halogenated aromatics such as fluorobenzene; halogenated alkylated aromatics such as trifluoromethylbenzene; nitrogen-containing aromatics such as nitrobenzene, benzonitrile, tolunitrile, pyridine, picoline, quinolone, isoquinoline, quinaldine, aniline and N-, N,N-alkylated aminoaromatics such as methylaniline, dimethylaniline, o-, m-, p-toluidine. The obtained products are the corresponding aminated arylamines or heteroarylamines. An especially preferred aromatic hydrocarbon is benzene which can be converted into aniline according to the process of the invention. Aniline can be used e.g. for the production of isocyanates, dyes and rubber processing chemicals.

In one embodiment, the amination occurs at a temperature between 400 and 700° C., preferably between 400 and 500° C., most preferably at a temperature around 450° C. Preferably, the amination occurs at a pressure between 50 and 150 bar, preferably at a pressure between 70 and 100 bar, more preferably at about 80 bar at the beginning of the reaction. Under these conditions a higher yield of the formed amine substituted aromatic compound can be obtained. During the amination, the pressure can vary and can be between 0 and 20 bar more or less then at the start of the amination. Typically, the pressure can vary with 10 bar more or less than the pressure at the beginning of the reaction.

Preferably, the amination process is performed in a batch-wise process, preferably in a continuous process. Suitable reactors are stirred tank reactors and tubular reactors. The relative amount of aromatic hydrocarbon and ammonia is dependent on which amination reaction is carried out. Stoichiometric amounts of the hydrocarbon and ammonia are generally used. But to shift the equilibrium to the product side, it is preferred to use one reactant in stoichiometric excess in the direct amination process. Preference is given to employ ammonia in stoichiometric excess.

The hydrocarbon and ammonia can be introduced in the reactor in gaseous or liquid form. The preferred phase is dependent on the used reaction condition and the employed reactants. In the preparation of aniline synthesized from benzene and ammonia, both reactants are preferably inserted as a liquid into the reactor. Inside the reactor, ammonia and benzene are gaseous and/or form a supercritical mixture.

In one embodiment, the amination occurs at weight hourly space velocity of between 0.5 and 1.5 $h^{-1}$, preferably between 0.6 and 1.0 $h^{-1}$, more preferably around 0.8 $h^{-1}$. Weight hourly space velocity (WHSV) is the flow rate of the aromatic hydrocarbon (in grams/hour) per mass of catalyst (in grams) used. It has been found that at such WHSV the yield of the aminated product increases compared to a WHSV that is higher than the preferred range.

The above characteristics, features and advantages of the present invention may become apparent from the following examples which illustrates by way of example the principles of the invention, without limiting the scope of the invention.

The present invention is described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

EXAMPLES

Reactor Set-Up and Experimental Procedure

A tubular reactor (length=31 cm, inner diameter=0.43 cm) is charged with 600 mg of catalyst in the center of the tube (particle size between 0.2-0.6 mm) and the remained space is filled up with carborundum. The catalyst bed has a length of 6.9 cm. The catalysts have been activated "in situ" prior to the amination catalytic reaction. The catalyst activation has been performed under air flow (190 ml/min) at 500° C. for 30, 60 or 120 min (examples 1,2,4,6 and 9) or under hydrogen flow (100% $H_2$, at 60 ml/min) at 450° C. for 90 min (examples 3 and 5) or at 200° C. for 60 or 80 min (examples 7, 8, 10). After that, the reactor is purged with nitrogen during 30 min and the temperature is brought to 450° C. Then ammonia is introduced to the reactor via a syringe pump to reach an internal pressure of 80 bar (±10 bar fluctuating during the reaction). After equilibrating the pressure, the reaction is started with a flow of 1.61 ml/h of ammonia (9.2 equiv., Linde 99.98%) and 0.565 ml/h of benzene (1.0 equiv., Aldrich 99.9%) added continuously to the system. The reaction is running 140 or 300 minutes. For each sample the reactor effluent is collected in methanol for 3 min at −2° C. using dodecane as an external GC standard. The sample is then analyzed by gas chromatography (VARIAN CP3800 with FID detector, HP5 column 30 m).

Synthesis of the VAPO Catalysts

The VAPO-5 support is prepared according to the literature (P.Concepción, J. M. López Nieto, J. Péres-Pariente *J. Mol. Catal. A: Chem.* 97 (1995) 173). In detail, 13 g of orthophosphoric acid (Aldrich, 85 wt %), 30 g of $H_2O$ miliQ and 6.7 g of pseudoboehmite (CATAPAL 70 wt % Al2O3) was stirred together for 2 h. 7.5 g of triethylamine (Aldrich 99 wt %) was slowly added under stirring and kept for another 2 h under stirring (Solution A). In a separate vessel, 2.5 g of triethylamine, 10 g of $H_2O$ miliQ and 1.2 g of $V_2O_5$ (Aldrich, 99.6 wt %) was mixed under stirring at 40° C. for ~1 h until complete dissolution of the vanadium salt (Solution B). Solution B was slowly added to solution A and kept for another 2 h under stirring. At this point, a homogenous gel is obtained with pH of ~5.6. The gel is introduced in 60 ml PTFE-lined stainless steel autoclaves and heated at 200° C. for 16 h. Afterwards, the autoclaves were quenched in cool water, centrifuged at 10,000 rpm, washed and dried at 80° C. The solid is calcined in air at 550° C. for 8 h in air. To reach the calcination temperature, the material is heated up in 2° C./min. The vanadium loading in the prepared VAPO-5 is 0.5 wt %. After this, wet impregnation techniques are applied to introduce the nickel and/or copper on the catalyst. An 7 wt % nickel loading was used in the VAPO-Ni samples (examples 4 and 5 in table 1), in detail, 296 mg $(Ni(OAc)_2(H_2O)_4)$(Panreac, 95 wt %) were dissolved in 5 ml water through slightly heating at 40° C. to prepare a salt solution. The solution was dropwise added under stirring on 1 g of VAPO-5. The final solid was dried at 100° C. for 12 h, followed by air calcination at 500° C./min for 8h with a heating rate of 2° C./min. In the VAPO-Ni,Cu samples (examples 6 to 8 in table 1) 7 wt % nickel and 3.5 wt % copper loading was used. In detail, (296 mg, 1.19 mmol) $(Ni(OAc)_2(H_2O)_4)$ (Panreac, 95%) and (128 mg, 0.28 mmol) $Cu(NO_3)_4(H_2O)_5$ (Aldrich 98%) were dissolved in 1.5 ml water through slightly heating at 40° C. to prepare a salt solution. The salt solution is then further used for impregnation of the VAPO sample. Afterwards the impregnated material is dried over night at 100° C. followed by air calcination at 500° C./min for 8 h with a heating rate of 2° C./min. The subsequent calcination is done "in situ" in the flow reactor according to the conditions set out in the table with a heating rate of 2° C./min.

Synthesis of the ALPO Catalyst

ALPO-5 was prepared according to the following receipt: 13 g of orthophosphoric acid (Aldrich, 85 wt %), 40 g of $H_2O$ miliQ and 6.7 g of pseudoboehmite (CATAPAL 70 wt % $Al_2O_3$) was stirred together for 2 h. After that, 10 g of triethylamine (Aldrich 99 wt %) was slowly added under stirring and kept for another 2 h under stirring. The gel is introduced in 60 ml PTFE-lined stainless steel autoclaves and heated for 200° C. for 16 h. After this, the autoclaves were quenched in cool water, centrifuged at 10,000rpm, washed and dried at 80° C. The solid is calcined in air at 550° C. for 8 h in air with a heating rate of 2° C./min. After this, wet impregnation techniques are applied to introduce the nickel and copper on the ALPO-5 sample. The synthetic procedure is the same as described above in the VAPO-5-NiCu samples using instead of VAPO-5, ALPO-5.

Comparative Example 1

The catalyst was prepared by coprecipitation techniques and includes Ni, Cu, Zr, and Mo as metal oxides. The catalyst was synthesized according to example 1 of US 2009/0292144 A1. The amination reaction of benzene occurred in the above described reaction set up. At 350° C. and 80 bar there was no aniline formed. However, by increasing the reaction temperature to 450° C. an average yield of 0.43% was obtained (see example 1 in table 1). The side products that are formed are toluene, benzonitrile, biphenyl and carbazole.

Comparative Examples 2-5

VAPO-5 prepared as described above was used in the reaction set up and procedure as described above.

The amination reaction occurred as described above in the experimental procedure of the patent.

VAPO-5 showed activity of the direct amination of benzene and aniline was formed (see example 2-5 in table 1). The activation of the catalyst in situ in the reactor with air or hydrogen did not change the results.

Also, VAPO-5 impregnated with nickel (prepared as described above) was used to aminate benzene in the reaction set up as describe above. The reaction occurred as described above in the experimental procedure of the patent.

It was found that by introducing nickel in VAPO, the maximum yield did not change but the average yield increased (see example 4 of table 1).

Examples 6-8

According to the Invention

Ni,Cu-VAPO-5 prepared as described above was used in the reaction set up and procedure as described above.

It is found that by impregnation of VAPO-5 with Ni and Cu, the activity of the catalyst increased, especially when the catalyst is reduced with hydrogen at 200° C. Reducing at 200° C. for 60 min, the yield reached was 1% at 140 minutes reaction time (see 7). Increasing the reduction time, from 60 min to 80 min, at the same temperature of 200° C., a maximum yield of 3.3% was formed at 160 minutes reaction time and an average yield of 1% was obtained. In addition, the selectivity of the reaction was very high. Carbazole, benzonitrile, biphenyl, toluene and diphenylamine are observed only in traces during the reaction. The calculation of the selectivity does not include the loss of benzene inside the reactor through coking or simple adsorption.

The catalyst has been regenerated by heating in-situ in air at 500° C. for 2 hours, then reducing in hydrogen at 200° C. for 80 minutes. After each cycle the catalyst was tested again using the procedure outlined above. It has been found that 9 regeneration cycles were completed successfully with no decrease in catalyst performance.

Example 9 and 10

According to the Invention

Common aluminophosphate impregnated with nickel and copper (see above) was used in the reaction set-up. The synthesis procedure and reaction set-up are as described above.

The AlPO material provided almost the same result with both hydrogen and air activation. Also the ALPO catalyst that was impregnated with Ni and Cu showed good results.

The invention claimed is:

1. A process for preparing aminated aromatic hydrocarbons comprising the steps of reacting an aromatic hydrocarbon with ammonia in the presence of a catalyst having a crystalline microporous structure wherein the catalyst comprises vanadium aluminophosphate molecular sieve (VAPO) and wherein the catalyst is impregnated with nickel and copper in amounts such that the nickel content is between 1 wt % and 30 wt % and the copper content is between 1 wt % and 30 wt %, based on the total weight of the catalyst.

2. The process according to claim 1, wherein the catalyst is treated by reduction or calcination.

3. The process according to claim 2, wherein the catalyst is reduced in the presence of molecular hydrogen.

4. The process according to claim 2, wherein the reduction with molecular hydrogen occurs at a temperature between 100 and 300° C.

5. The process according to claims 2, wherein the reduction with molecular hydrogen occurs during between 50 and 100 minutes.

6. The process according to claim 2, wherein the calcination with air occurs at a temperature between 400 and 700° C.

7. The process according to claim 1, wherein the catalyst has a framework type code provided by the International Zeolite Association selected from the group consisting of AFI, AEL, ATO, AEI, AET, AFN, AFO, AFT, ATV, CHA, ERI, LEV, SOD, and VFI.

8. The process according to claim 1, wherein the aromatic hydrocarbon is benzene.

TABLE 1 results of experiments in examples 1-10

| Sample | catalyst | WHSV | treatment of catalyst | reaction condition | average yield, highest yield | selectivity |
|---|---|---|---|---|---|---|
| 1* | Ni, CU, Zr, Mo | 0.83 h$^{-1}$ | Air at 500° C. | 450° C., 80 bar | 0.43%, 0.88% | 90% |
| 2** | VAPO-5 | 0.83 h$^{-1}$ | Air at 500° C., 2 h | 450° C., 80 bar | 0.05%, 0.15% | 69% |
| 3** | VAPO-5 | 0.83 h$^{-1}$ | H$_2$ at 450° C., 1.5 h | 450° C., 80 bar | 0.06%, 0.15% | 63% |
| 4** | VAPO-Ni | 0.83 h$^{-1}$ | Air at 500° C. 30 min | 450° C., 80 bar | 0.09%, 0.14% | 67% |
| 5** | VAPO-Ni | 0.83 h$^{-1}$ | H$_2$ at 450° C. 1.5 h | 450° C., 80 bar | <0.01%, 0.03% | 67% |
| 6 | VAPO-Ni, Cu | 0.83 h$^{-1}$ | Air at 500° C. 60 min | 450° C., 80 bar | 0.06%, 0.11% | 56% |
| 7 | VAPO-Ni, Cu | 0.83 h$^{-1}$ | H$_2$ at 200° C. 60 min | 450° C., 80 bar | 0.66%, 1.01% | 89% |
| 8 | VAPO-Ni, Cu | 0.83 h$^{-1}$ | H$_2$ at 200° C. 80 min | 450° C., 80 bar | 0.98%, 3.31% | 92% |
| 9 | AlPO-Ni, Cu | 0.83 h$^-$ | Air at 500° C. 60 min | 450° C., 80 bar | 0.85%, 1.52% | 88% |
| 10 | AlPO-Ni, Cu | 0.83 h$^-$ | H$_2$ at 200° C. 80 min | 450° C., 80 bar | 0.52%, 1.47% | 87% |

*comparative example. Catalyst prepared according to example 1 of US 2009/0292144 A1;
**comparative examples; WHSV is the weight hourly space velocity 9. The process according to claim 1, wherein the catalysts are treated at a temperature between 350 and 700° C.

10. The process according to claim 1, wherein the amination occurs at a temperature between 400 and 700° C.

11. The process according to claim 1, wherein the amination occurs at a pressure between 50 and 150 bar.

12. The process according to claim 1, wherein the aromatic hydrocarbon is substituted.

* * * * *